United States Patent
Ito et al.

(10) Patent No.: US 11,168,137 B2
(45) Date of Patent: Nov. 9, 2021

(54) METHOD FOR REDUCING SIDE EFFECTS OF IMMUNE CHECKPOINT CONTROL AGENT

(71) Applicants: IDAC THERANOSTICS, INC., Tokyo (JP); THE UNIVERSITY OF TOKYO, Tokyo (JP)

(72) Inventors: Satoru Ito, Tokyo (JP); Shoji Yokochi, Tokyo (JP); Kouji Matsushima, Tokyo (JP); Satoshi Ueha, Tokyo (JP); Yoshiro Ishiwata, Tokyo (JP)

(73) Assignees: IDAC THERANOSTICS, INC., Tokyo (JP); THE UNIVERSITY OF TOKYO, Tokyo (JP)

( * ) Notice: Subject to any disclaimer, the term of this patent is extended or adjusted under 35 U.S.C. 154(b) by 189 days.

(21) Appl. No.: 15/316,592

(22) PCT Filed: Jun. 10, 2015

(86) PCT No.: PCT/JP2015/066790
§ 371 (c)(1),
(2) Date: Dec. 6, 2016

(87) PCT Pub. No.: WO2015/190538
PCT Pub. Date: Dec. 17, 2015

(65) Prior Publication Data
US 2017/0145099 A1    May 25, 2017

(30) Foreign Application Priority Data

Jun. 11, 2014 (JP) .............................. JP2014-120245
Sep. 3, 2014 (JP) .............................. JP2014-178909

(51) Int. Cl.
C07K 16/28 (2006.01)
A61K 39/395 (2006.01)
A61K 39/00 (2006.01)

(52) U.S. Cl.
CPC ........ *C07K 16/2812* (2013.01); *A61K 39/395* (2013.01); *C07K 16/2818* (2013.01); *C07K 16/2827* (2013.01); *C07K 16/2878* (2013.01); *A61K 2039/505* (2013.01); *A61K 2039/507* (2013.01); *C07K 2317/24* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| 8,399,621 | B2 * | 3/2013 | Nakagawa | C07K 16/2812 424/144.1 |
|---|---|---|---|---|
| 9,156,912 | B2 | 10/2015 | Matsushima et al. | |
| 10,746,726 | B2 | 8/2020 | Matsushima et al. | |
| 2010/0310573 | A1 | 12/2010 | Nakagawa et al. | |
| 2012/0027748 | A1 | 2/2012 | Matsushima et al. | |
| 2015/0353637 | A1 * | 12/2015 | Wang | G01N 33/6863 424/139.1 |
| 2017/0007698 | A1 * | 1/2017 | Kim | A61K 39/0011 |

FOREIGN PATENT DOCUMENTS

| JP | WO2010/074266 A1 | 6/2012 |
|---|---|---|
| WO | WO 2011/109789 A2 | 9/2011 |
| WO | WO 2015/120198 A1 | 8/2015 |

OTHER PUBLICATIONS

Ruuls et al. (Biotechnol. J. 2008, 3, 1157-1171). (Year: 2008).*
Liu et al., Clinical & Translational Immunology (2014) 3, e22. (Year: 2014).*
Natsume et al. (Drug Design, Development and Therapy 2009:3 7-16). (Year: 2009).*
Kim et al. (Blood. 2007;109:4655-4662). (Year: 2007).*
Van der Lubbe et al. (Scand J. Immunol. 39, 286-294, 1994. (Year: 1994).*
Cardarelli et al. (Cancer Immunol Immunother (2010) 59:257-265. (Year: 2010).*
Murphy et al. (Blood. 2014;123(14):2172-2180, and Supplement pp. 1-11). (Year: 2014).*
Rakhmilevich et al. (Clin Cancer Res. Apr. 2001;7(4):952-61). (Year: 2001).*
Shvarts et al. (Urology 68: 1132-1138, 2006). (Year: 2006).*
Dourado et al. (Cellular Immunology 270 (2011) 198-206). (Year: 2011).*
Callahan et al., "Anti-CTLA-4 Antibody Therapy: Immune Monitoring During Clinical Development of a Novel Immunotherapy," Semin. Oncol. (Oct. 2010), vol. 37, No. 5, pp. 473-484.
Choi et al., "Mechanisms Involved in Synergistic Anticancer Immunity of Anti-4-1BB and Anti-CD4 Therapy," Cancer Res. (2007), vol. 67, No. 18, pp. 8891-8899.
D'Amore et al., "Phase II trial of zanolimumab (HuMax-CD4) in relapsed or refractory non-cutaneous peripheral T cell lymphoma," British Journal of Haematology (2010), vol. 150, pp. 565-573.
Extended European Search Report dated Nov. 20, 2017, in European Patent Application No. 15807493.0.

(Continued)

*Primary Examiner* — Zachary S Skelding
(74) *Attorney, Agent, or Firm* — Birch, Stewart, Kolasch & Birch, LLP (57) ABSTRACT

Disclosed is a means for reducing side effects of an immune checkpoint regulator that is used as an anticancer drug or the like. A side-effect reducing agent according to the present invention comprises as an effective ingredient an anti-CD4 antibody having a high cytotoxic activity, or an anti-CD4 antibody or antigen-binding fragment thereof which antibody or fragment comprises a cytotoxic component bound thereto. The anti-CD4 antibody is a human-type chimeric antibody, humanized antibody or human antibody against human CD4. The immune checkpoint regulator may be, for example, an anti-PD-L1 antibody, an antagonistic anti-CTLA-4 antibody, or an agonistic anti-OX40 antibody.

15 Claims, 6 Drawing Sheets

(56) References Cited

OTHER PUBLICATIONS

Ito et al., "Abstract 4126: An anti-CD4 antibody protects mice from anti-PD-1/PDL-1 antibody induced fatal anaphylaxis and shows potent anti-metastatic activity in the 4T1 spontaneous metastasis model," Cancer Res.(Jul. 2016), vol. 76, No. 14 sup, pp. 1-4.

Wang et al., "Foxp3+T Cells Inhibit Antitumor Immune Memory Modulated by mTOR Inhibition," Cancer Res. (2014), vol. 74, No. 8, pp. 2217-2228.

Wolchok, J. D. and Y. Saenger, "The Mechanism of Anti-CDLA-4 Activity and the Negative Regulation of T-Cell Activation," The Oncologist (2008), vol. 13, Suppl. 4, pp. 2-9.

Cote, Anik L. et al., "Protective CD8 Memory T Cell Responses to Mouse Melanoma Are Generated in the Absence of CD4 T Cell Help", Plos One, vol. 6, Issue 10, Oct. 2011, pp. 1-10.

Yu, Ping et al., "Intratumor depletion of CD4+ cells unmasks tumor immunogenicity leading to the rejection of late-stage tumors", The Journal of Experimental Medicine, vol. 201, No. 5, Mar. 7, 2005, pp. 779-791.

U.S. Office Action for U.S. Appl. No. 16/234,292, dated Aug. 9, 2021 (Non-Final Rejection).

Yamane-Ohnuki et al., "Production of therapeutic antibodies with controlled fucosylatios", mAbs, vol. 1, Issue 3, 2009, pp. 230-236.

Croce et al., "Transient depletion of CD4+ T cells augments IL-21-based immunotherapy of disseminated neuroblastoma in syngeneic mice", International Journal of Cancer (127), pp. 1141-1150, 2010.

Hendrzak-Henion et al., "Role of the Immune System in Mediating the Antitumor Effect of Benzophenothiazine Photodynamic Therapy". Photochemistry and Photobiology, 69(5), pp. 575-581, 1999.

Herzyk et al., "Immunomodulatory Effects of Anti-CD4 Antibody in Host Resistance against Infections and Tumors in Human CD4 Transgenic Mice", Infection and Immunity, vol. 69, No. 2. pp. 1032-1043, 2001.

Rakhmilevich et al., "Elimination of CD4+ T cells in mice bearing an advanced sarcoma augments the antitumor action of interleukin-2". Cancer Immunology Immunotherapy (38), pp. 107-112, 1994.

U.S. Appl. No. 16/234,292, filed Dec. 27, 2018.

* cited by examiner

METHOD FOR REDUCING SIDE EFFECTS OF IMMUNE CHECKPOINT CONTROL AGENT

TECHNICAL FIELD

The present invention relates to a method for reducing side effects of an immune checkpoint regulator.

BACKGROUND ART

Recently, cancer immunotherapy is often reported in the news. In 2013 and 2014, this news has filled the pages in American Society of Clinical Oncology. Thanks to the progress of genome analysis, effects of drugs in individual patients can now be clearly discussed in relation to their oncogene abnormalities. However, in spite of such linking between gene abnormalities and effects of drugs, there still remains a problem: what therapeutic strategies can be proposed for patients to whom such links are not applicable? Unlike existing carcinostatic drugs (including molecularly-targeted drugs), which directly target cancers, cancer immunotherapy is a therapeutic method which targets the immune cell system. That is, gene mutations involved in carcinogenesis do not have direct correlation with effects of drugs. Similarly, however, it is becoming clear that cancer immunotherapy is not necessarily effective for all patients. Research and development of means for increasing its effectiveness are urgent issues, and therapeutic methods aiming at combined effects and synergistic effects of different types of drugs are being developed. FDA, as well as PMDA, which is an assessment agency in Japan, is quickly preparing guidelines on clinical trials in consideration of the combination therapies.

Conventional carcinostatic drugs are means which directly target cancer cells, and also affect normal cells. They are therefore known to impose heavy burdens on patients, and to cause serious side effects. In spite of this, priority was given to the actual life-prolonging effect rather than reduction of the side effects, so that patients could not be satisfied with those drugs. Recent interest has focused on cancer immunotherapy, but, since cancer peptide vaccines were found to be effective for only limited patients, attempts have been made to discover other means. That is, development of immunotherapies, in particular, development of antibody drugs targeting molecules involved in the immune system, has been intensively carried out in recent years. Although they do not have a remarkable effect in terms of reduction of the tumor size, they are attracting attention from the viewpoint of the fact that they have characteristic life-prolonging effects.

An anti-CTLA-4 antibody has already been approved by the FDA in the United States. An anti-PD-1 antibody is now being developed, and has been applied for its approval. Since both CTLA-4 and PD-1 molecules are understood as molecules having functions to act at immune checkpoints, antibodies against these molecules are recognized as immune checkpoint inhibitors (Non-patent Document 1). However, during their clinical development, various serious side effects have been found so far (Non-patent Document 2). These side effects are autoimmune disease-like side effects in some aspects, and qualitatively different from side effects caused by conventional carcinostatic drugs due to their non-specific attack to normal cells. From the viewpoint of the fact that control of "cancer", a phenomenon which directly threatens the life, should have the highest priority, means for control of cancer that are accompanied by serious side effects are still selected as long as they produce therapeutic effects. Nevertheless, side effects are not preferred from the patients' standpoint. Thus, means for reducing side effects as much as possible are desired. There are several options for the reduction of side effects, for example, to reduce the dose of the drug, to administer the drug to only patients in whom the drug can be expected to be effective by means of the personalized medicine, to select a drug whose side effects can be reduced by combination with another drug, and so on.

Also in the field of carcinostatic drugs, the advent of molecular-targeted drugs has allowed development of anti-cancer drugs having less side effects compared to existing carcinostatic drugs. However, negative actions on the body still cannot be avoided. In spite of the progress in research and development of peptide cancer vaccines as part of immunotherapy, the effects of these vaccines are relatively low (that is, the frequency of patients showing effectiveness of the vaccines is low), so the vaccines are not drawing much attention at present. More recently, antibody drugs (for example, Herceptin, an antibody against the molecule called her2/neu) have become available, and they attracted attention as molecular-targeted drugs which are not synthetic pharmaceuticals. However, their problems such as recurrence and drug resistance are also becoming apparent. After the advent of such binding-inhibitory antibodies, patients placed their hope on effectiveness of those antibodies, but the antibodies have showed only slight life-prolonging effects so far.

Under such circumstances, immune checkpoint inhibitors/activators have appeared as antibody drugs. For example, an antibody targeting CTLA-4 (molecule expressed on the regulatory T-cell subset) does not have much tumor regression effects on melanoma, which is known to be a cancer having relatively strong immunogenicity, but has been found to allow significant prolongation in terms of the survival rate. Thus, this antibody is now attracting great attention (Non-patent Document 3). It is understood that they cancel the immunosuppressive state of the cancer to enhance an environment in which cytotoxic immune cells can be active. Another example of such molecules is the PD-1 molecule. An antibody drug targeting this molecule has a remarkable effect, and it has been found to be even effective for about 30% of patients with solid cancer (for example, lung cancer) (Non-patent Document 2).

An anti-CTLA-4 antibody, which was already approved in the United States (ipilimumab; trade name, Yervoy), has been reported to have side effects including autoimmune disease-like symptoms and symptoms similar to their related symptoms (Non-patent Document 4). Among them, dermatitis, hepatitis, enteritis, hypophysis, and uveitis are well-known side effects, and Grade 1 to Grade 4 have been reported as the degrees of the side effects. Caution is required since there are lethal cases of the Grade-4 enteritis. Similar side effects have been reported for the anti-PD-1 antibody, and in addition, this antibody has also been reported to cause damage to the respiratory system, which is not reported in the above-described cases (Non-patent Document 5). In clinical trial cases of an anti-PD-L1 antibody, hypothyroidism, endophthalmitis, and myasthenia have been reported (Non-patent Document 6). An anti-CD28 antibody had been developed for targeting also B-cell chronic lymphocytic leukemia. However, the approval for carrying out its clinical trial has been canceled because of occurrence of multiple organ failure, which is a serious accident from the viewpoint of safety, during the test (Non-patent Document 9). The target molecule CD28 is also an immune checkpoint molecule, and has an agonistic action.

As simple approaches for reduction of these side effects, reduction of the dose, reduction of the frequency of administration (Non-patent Document 7), use of local administration instead of systemic administration (Non-patent Document 8), etc. have been attempted, but these cannot be said to be essential approaches. More essential solutions are demanded.

PRIOR ART DOCUMENT(S)

Non-Patent Document(s)

Non-patent Document 1: Pardoll D M. The blockade of immune checkpoints in cancer immunotherapy. Nature reviews Cancer. 2012; 12(4): 252-64.
Non-patent Document 2: Hamid O, Robert C, Daud A, Hodi F S, Hwu W J, Kefford R, et al. Safety and tumor responses with lambrolizumab (anti-PD-1) in melanoma. The New England journal of medicine. 2013; 369(2): 134-44.
Non-patent Document 3: Prieto P A, Yang J C, Sherry R M, Hughes M S, Kammula U S, White D E, et al. CTLA-4 blockade with ipilimumab: long-term follow-up of 177 patients with metastatic melanoma. Clinical cancer research: an official journal of the American Association for Cancer Research. 2012; 18(7): 2039-47.
Non-patent Document 4: Della Vittoria Scarpati G, Fusciello C, Perri F, Sabbatino F, Ferrone S, Carlomagno C, et al. Ipilimumab in the treatment of metastatic melanoma: management of adverse events. OncoTargets and therapy. 2014; 7: 203-9.
Non-patent Document 5: Topalian S L, Hodi F S, Brahmer J R, Gettinger S N, Smith D C, McDermott D F, et al. Safety, activity, and immune correlates of anti-PD-1 antibody in cancer. The New England journal of medicine. 2012; 366(26): 2443-54.
Non-patent Document 6: Brahmer J R, Tykodi S S, Chow L Q, Hwu W J, Topalian S L, Hwu P, et al. Safety and activity of anti-P D-L1 antibody in patients with advanced cancer. The New England journal of medicine. 2012; 366(26): 2455-65.
Non-patent Document 7: Camacho L H, Antonia S, Sosman J, Kirkwood J M, Gajewski T F, Redman B, et al. Phase I/II trial of tremelimumab in patients with metastatic melanoma. Journal of clinical oncology: official journal of the American Society of Clinical Oncology. 2009; 27(7): 1075-81.
Non-patent Document 8: Sandin L C, Eriksson F, Ellmark P, Loskog A S, Totterman T H, Mangsbo S M. Local CTLA4 blockade effectively restrains experimental pancreatic adenocarcinoma growth in vivo. Oncoimmunology. 2014; 3(1): e27614.
Non-patent Document 9: Suntharalingam G, Perry M R, Ward S, Brett S J, Castello-Cortes A, Brunner M D, Panoskaltsis N. The New England journal of Medicine. 2006; 355(10): 1018-28.

SUMMARY OF THE INVENTION

Problems to be Solved by the Invention

An object of the present invention is to provide means for reducing side effects of an immune checkpoint regulator.

Means for Solving the Problems

In the beginning of the study, the present inventors investigated the behavior of immune checkpoint antibodies in a mouse model. In this study, an anti-CD4 antibody whose anticancer action has already been found in our group was used. To provide a negative control for the experiment system, a comparative experiment was carried out using untreated mice (or mice to which a nonspecific IgG was administered). As a result, cases of death (non-tumor death) were found to occur earlier in the groups receiving administration of an immune checkpoint antibody than in the negative control. The non-tumor death was especially remarkable in mice receiving an anti-CTLA-4 antibody, anti-OX40 antibody, anti-PD-1 antibody, or anti-PD-L1 antibody. On the other hand, since the cancer regulation capacity of the anti-CD4 antibody was excellent, combinations of the anti-CD4 antibody with these immune checkpoint antibodies were studied, expecting combined effects. As a result, non-tumor death was suppressed by any of the combinations, and remarkable life-prolonging effects could be observed. Although this is an effect observed in the mouse model, the survival rate was higher than that observed with the combination of an anti-CTLA-4 antibody and anti-PD-1 antibody whose clinical trial data have been published. That is, by the combinations with the anti-CD4 antibody, deaths caused by side effects could be totally canceled, and a higher survival rate than that in the negative control could be achieved.

The present inventors succeeded in establishment of a humanized anti-CD4 antibody capable of widely eliminating CD4-positive cells and having strong cytotoxic activity, and intensively carried out a model-mouse-level study as described above aiming at development of means which produces a wide range of effects by combinations of drugs based on the above antibody, thereby accomplishing the present invention.

That is, the present invention provides a side-effect reducing agent for an immune checkpoint regulator, said side-effect reducing agent comprising as an effective ingredient an anti-CD4 antibody having a high cytotoxic activity, or an anti-CD4 antibody or antigen-binding fragment thereof which antibody or fragment comprises a cytotoxic component bound thereto, wherein said anti-CD4 antibody is a human-type chimeric antibody, humanized antibody or human antibody against human CD4. The present invention also provides a method for reducing a side effect(s) of an immune checkpoint regulator, said method comprising administering to a patient an effective amount of an anti-CD4 antibody having a high cytotoxic activity, or an anti-CD4 antibody or antigen-binding fragment thereof which antibody or fragment comprises a cytotoxic component bound thereto, wherein said anti-CD4 antibody is a human-type chimeric antibody, humanized antibody, or human antibody against human CD4.

Effect of the Invention

According to the present invention, by using a humanized anti-CD4 antibody or the like that can sufficiently exert cytotoxic activity against CD4-positive cells in the human body, side effects caused by immune checkpoint regulators that are used as anticancer drugs or the like can be reduced.

MODE FOR CARRYING OUT THE INVENTION

The side-effect reducing agent for an immune checkpoint regulator according to the present invention comprises any of the followings as an effective ingredient. Both of them may be used in combination. In the present specification, the effective ingredients (1) and (2) may be hereinafter collectively referred to as "anti-CD4 component".
(1) An anti-CD4 antibody having a high cytotoxic activity.
(2) An anti-CD4 antibody or antigen-binding fragment thereof, comprising a cytotoxic component bound thereto.

In both cases of (1) and (2), the anti-CD4 antibody is typically an antibody against human CD4, and is a human-type antibody, a humanized antibody (prepared by transplanting the CDR region of a non-human-derived antibody to the corresponding region of a human antibody), or a human antibody (the same antibody as an antibody produced in the body of human, which is prepared using a non-human animal or a human cell line).

The cytotoxic activity antibodies have includes the antibody-dependent cell-mediated cytotoxicity activity (ADCC activity) and the complement-dependent cytotoxicity activity (CDC activity). In cases where the anti-CD4 component belongs to (1) above, the anti-CD4 antibody may have any of the ADCC activity and the CDC activity. It is necessary to use an antibody having a high cytotoxic activity that can exert a sufficiently high ability to kill CD4-positive cells.

The term "high cytotoxic activity" in the context of the ADCC activity means that an antibody has a higher ADCC activity than the known anti-CD4 antibody 6G5 or CE9.1 that is known to have an ADCC activity, when the ADCC activity against CD4-expressing cells is measured by a known measurement method. In the context of the CDC activity, the term means that an antibody has a stronger CDC activity than the known anti-CD4 antibody OKT4 that is known to have a CDC activity, when the CDC activity against CD4-expressing cells is measured in an experimental system using the same complements by a known measurement method.

Methods for measurement of the ADCC activity and the CDC activity of antibodies are known and described in e.g. Cancer Immunol. Immunother, 36, 373 (1993), and kits therefor are commercially available. Whether a given antibody has a higher cytotoxic activity than known anti-CD4 antibodies or not may be evaluated using such a commercially available kit. A specific example of measurement of the cytotoxic activity using a commercially available kit is described in the Examples below. The level of the ADCC activity of a given anti-CD4 antibody can also be evaluated by mixing human peripheral blood mononuclear cells with the given anti-CD4 antibody, allowing the reaction to proceed at 37° C. for several hours, performing flow cytometry analysis to measure $CD3^+$ cells and $CD8^+$ cells, calculating the ratio of $CD8^+$ cells to $CD3^+$ cells ($CD8^+$ cells/$CD3^+$ cells) or the ratio of $CD3^+$ cells to $CD8^+$ cells ($CD3^+$ cells/$CD8^+$ cells) in the reaction solution, and then comparing the calculated ratio with a ratio calculated from measurement on a reaction solution in which an anti-CD4 antibody having no ADCC activity or a known anti-CD4 antibody described above is used. As the ADCC activity increases, the number of $CD4^+$ cells in the reaction solution decreases. In peripheral blood, the sum of the number of $CD4^+$ cells and the number of $CD8^+$ cells is almost the same as the number of $CD3^+$ cells. Accordingly, the calculated value of $CD8^+$ cells/$CD3^+$ cells in the reaction solution increases as the number of $CD4^+$ cells decreases, and the calculated value of $CD3^+$ cells/$CD8^+$ cells in the reaction solution decreases as the number of $CD4^+$ cells decreases.

Preferably, an anti-CD4 antibody having a high cytotoxic activity has an ADCC activity that is 10 times or more, more preferably 100 times or more higher than the ADCC activity of the known anti-CD4 antibody 6G5 and/or CE9.1, or has a CDC activity that is 10 times or more, more preferably 100 times or more higher than the CDC activity of the known anti-CD4 antibody OKT4. As used herein, the term "10 times or more" means, for example, that the minimum antibody concentration at which a given antibody exhibits a cytotoxic activity against a certain amount of cells is onetenth or less of that of the above-described known antibody. As for the affinity of the anti-CD4 antibody to CD4, the antibody binding activity $K_D$ may be about $1 \times 10^{-9}$ M or less.

An anti-CD4 antibody having a high cytotoxic activity can be prepared, for example, from a monoclonal anti-CD4 antibody prepared by a known method or from an already established known anti-CD4 antibody, by increasing the cytotoxicity of the antibody by a method known in the art. In cases where an anti-CD4 antibody that specifically recognizes CD4 expressed on the cell surface and has a strong cytotoxicity is known, such an antibody may be used as an effective ingredient of the agent of the present invention. For example, WO 2010/074266 discloses an anti-CD4 antibody having a higher ADCC activity than conventional anti-CD4 antibodies.

A method per se of producing a monoclonal antibody is a well-known conventional method in the art. For example, when carrying out the well-known hybridoma method, an anti-CD4 monoclonal antibody can be obtained by immunizing an animal (except human) with a CD4 protein or an appropriate fragment thereof (the extracellular region, e.g., a region from the N-terminus to the 394th amino acid of CD4), collecting antibody-producing cells such as spleen cells or lymphocytes from the immunized animal, fusing the antibody-producing cells with myeloma cells to prepare hybridomas, screening a hybridoma which produces an antibody that binds to CD4 protein, growing the hybridoma, and then collecting an anti-CD4 antibody from the culture supernatant. The gene sequence, amino acid sequence, spatial structure, and the like of CD4 have been deposited in public databases under the accession numbers of, for example, M12807 in GenBank of NCBI. The CD4 protein or an appropriate fragment thereof to be used as an immunogen can be easily prepared based on such sequence information according to well-known genetic engineering methods.

Methods for preparing a chimeric antibody, humanized antibody, or human antibody have been also established as well-known methods in the art. For example, an anti-CD4 human antibody can be prepared by using CDR sequence fragments that ensure CD4 recognition prepared by cassette modification method.

Methods for increasing the cytotoxicity of an antibody are also known, and any of these methods may be used. An example of the known methods is described below.

One method for increasing the ADCC activity is the POTELLIGENT (registered trademark) technology, in which fucose (core fucose) contained in sugar chains present in the Fc region of the antibody is removed (Yamane-Ohnuki N, Satoh M, Production of therapeutic antibodies with controlled fucosylation, MAbs2009; 1: 230-236). The enzyme that adds core fucose is encoded by the gene named FucT-8 (Fut-8). Therefore, antibody molecules with enhanced ADCC activity can be obtained by expressing the gene encoding a recombinant antibody in Fut-8 knockout animal cells (Yamane-Ohnuki N, et al., Establishment of FUT8 knockout Chinese hamster ovary cells: an ideal host cell line for producing completely defucosylated antibodies with enhanced antibody-dependent cellular cytotoxicity, Biotechnol Bioeng 2004; 87: 614-622). A method in which fucose substrate donation is blocked is also known, but this method removes all fucose including core fucose, and hence is not specific to core fucose. Thus, the POTELLIGENT (registered trademark) technology described above is more preferred.

Another example of the method for increasing the ADCC activity is a method in which sugar chains present in the Fc region of the antibody is converted. In this method, addition of core fucose is avoided by introduction of GlcNAc in the antenna-type branched sugar chain region by GnT-III gene manipulation (M. Schuster et al., Improved effector functions of a therapeutic monoclonal Lewis Y-specific antibody by glycoform engineering, Cancer Res 2005; 65: 7934-7941). An anti-CD4 antibody having enhanced ADCC activity prepared by such a method may also be used.

A known example of the method for enhancing the CDC activity is the COMPLEGENT (registered trademark) technology, wherein a part of isotype IgG1 is combined with the sequence of isotype IgG3 to increase the CDC activity (Natsume A, In M, Takamura H, et al. Engineered antibodies of IgG1/IgG3 mixed isotype with enhanced cytotoxic activities, Cancer Res. 2008; 68: 3863-3872).

Another known example is the AccretaMab (registered trademark) technology, wherein the POTELLIGENT (registered trademark) technology and the COMPLEGENT (registered trademark) technology described above are employed in combination to strongly increase the cytotoxic activity of an antibody (Natsume A, et al., Improving effector functions of antibodies for cancer treatment: Enhancing ADCC and CDC, Drug Des Devel Ther. 2009; 3: 7-16). An anti-CD4 antibody wherein both ADCC activity and CDC activity are increased by such a method may also be used.

In cases where an anti-CD4 antibody to which a cytotoxic component is bound is used, the antibody does not need to have a high cytotoxic activity, because CD4-positive cells are injured by the cytotoxic component. An antibody fragment retaining the binding capacity to CD4 (antigen-binding fragment), comprising a cytotoxic component bound thereto may also be used as an effective ingredient of the agent of the present invention.

In the present invention, the cytotoxic component means a substance having an activity to destroy living cells, and includes biological toxic substances, chemical substances, and radioactive substances.

The antigen-binding fragment may be any antibody fragment as long as it retains the binding capacity (antigen-antibody reactivity) to the corresponding antigen of its original antibody. Specific examples of the antigen-binding fragment include, but are not limited to, Fab, F(ab')$_2$, and scFv. Fab and F(ab')$_2$ can be obtained, as is well known, by treatment of a monoclonal antibody with a protease such as papain or pepsin. Methods for preparing scFv (single chain fragment of variable region) are also well known. For example, scFv can be obtained by extracting mRNA from a hybridoma prepared as described above, preparing single-stranded cDNA, performing PCR using primers specific to the immunoglobulin H chain and L chain to amplify the immunoglobulin H-chain gene and L-chain gene, linking these using a linker, giving an appropriate restriction enzyme site(s) to the resulting product, introducing the product into a plasmid vector, transforming *E. coli* with the resulting vector to allow expression of scFv, and then recovering the expressed scFv from *E. coli*.

In the present invention, "immune checkpoint regulator" means a substance that promotes activation of T cells by regulating a function of an immune checkpoint molecule. The term "immune checkpoint molecule" includes both receptors and ligands that function as an immune checkpoint.

Immune checkpoints are the immune escape mechanism to prevent the immune system from attacking its own body. Immune checkpoint receptors are present on T cells, and interact with ligands expressed on antigen-presenting cells. T cells recognize an antigen presented on the MHC molecule and are activated to generate an immune reaction, whereas the activation of T cells is controlled by an interaction between immune checkpoint receptor and ligand that occurs in parallel. Immune checkpoint receptors include co-stimulatory receptors and inhibitory receptors, and the T cell activation and the immune reaction are controlled by a balance between both receptors.

An immune checkpoint regulator is typically used as an anticancer drug. Thus, the side-effect reducing agent of the present invention is typically an agent for reducing side effects of an anticancer drug whose action is based on regulation of an immune checkpoint. Cancer cells express a ligand for an inhibitory immune checkpoint receptor, and escape from attack of cytotoxic T cells utilizing the receptor. Therefore, administration of an antagonist against the inhibitory receptor can prevent cancer cells from utilizing the immune checkpoint mechanism, thereby facilitating killing of cancer cells by $CD8^+$ T cells. In addition, administration of an agonist against a co-stimulatory immune checkpoint receptor can enhance the immune reaction, by which killing of cancer cells by $CD8^+$ T cells can also be facilitated.

As anticancer drugs based on regulation of immune checkpoints, an anti-CTLA-4 antibody, anti-PD-1 antibody, anti-PD-L1 antibody and the like are being developed for melanoma, lung cancer, leukemia, gastric cancer, lymphoma, renal cancer, and the like. However, such immune checkpoint antibodies are known to have side effects such as autoimmune disease-like side effects, and lethal cases have also been reported. By using an anti-CD4 component in combination with an immune checkpoint regulator, such serious side effects can be reduced, and the life-prolonging effect of an anticancer drug based on immune checkpoint regulation can be enhanced. The effect to reduce side effects can be obtained regardless of when combined use of the anti-CD4 component is started, not only by starting the combined use at an early stage after onset of the treatment with immune checkpoint regulator, but also at any other stages. Also in the future, anticancer drugs based on regulation of immune checkpoints will be developed for various cancers including solid cancers and blood cancers. If the problem of side effects is solved by the present invention, practical application of those anticancer drugs may be largely promoted. Details of the mechanism of the reduction of side effects of immune checkpoint regulators by anti-CD4 components are not clear. Although the scope of the present invention is not bound by theories, the following mechanism can be assumed. As side effects caused by immune checkpoint regulators, autoimmune disease-like symptoms are known. On the other hand, the following Example 4 shows that a side effect of immune checkpoint antibodies found in a 4T1 tumor-bearing mouse model is anaphylaxis. Autoimmune disease-like symptoms have the same mechanism as that of allergic reactions. It is thought that removal of CD4-positive immune cells from the body by administration of an anti-CD4 component suppresses generation or action of factors (for example, excessively responding T cells) that may be involved in occurrence of the above symptoms, resulting in the reduction of the side effects.

In the present invention, the term "antagonist" includes various substances that interfere with receptor activation induced by binding between receptor and ligand. Examples thereof include substances that interfere with the binding between receptor and ligand by binding to the receptor, and substances that interfere with the binding between receptor and ligand by binding to the ligand.

For example, "an antagonist against an inhibitory immune checkpoint molecule" may be an antagonistic antibody that binds to an inhibitory immune checkpoint molecule (inhibitory receptor or its ligand), a soluble polypeptide that is designed based on an inhibitory immune checkpoint ligand and does not activate the receptor, or a vector capable of expressing the polypeptide, or the like. Examples of the inhibitory immune checkpoint molecule include receptors such as PD-1, CTLA-4, LAG-3, TIM-3, and BTLA, and ligands such as PD-L1 (ligand for PD-1), PD-L2 (ligand for PD-1), GAL9 (ligand for TIM-3), and HVEM (ligand for BTLA). Methods of producing an antibody, and methods of producing a polypeptide by chemical synthesis or genetic engineering procedure are well-known conventional methods in the art, and a skilled person can prepare an antagonist against an inhibitory immune checkpoint molecule as described above by conventional methods.

"An agonist against a co-stimulatory immune checkpoint molecule" may be an agonistic antibody that binds to a co-stimulatory immune checkpoint receptor, a soluble polypeptide that is designed based on a co-stimulatory immune checkpoint ligand and has an effect to activate the receptor, or a vector capable of expressing the polypeptide, or the like. Examples of the co-stimulatory immune checkpoint molecule include receptors such as CD137, OX40, and GITR, and ligands such as CD137L (ligand for CD137), OX40L (ligand for OX40), and TNFSF18 (ligand for GITR).

The immune checkpoint molecule targeted by the immune checkpoint regulator may be, for example, at least one selected from CTLA-4, PD-L1, OX40, PD-1, LAG-3, TIM-3, BTLA, and GITR; at least one selected from CTLA-4, PD-L1, OX40, and PD-1; at least one selected from the group consisting of CTLA-4, PD-L1, OX40, BTLA, GITR, LAG-3, and TIM-3; at least one selected from CTLA-4, PD-L1, and OX40; or at least one selected from the group consisting of BTLA, GITR, LAG-3, and TIM-3. It has been concretely confirmed that, among anti-immune checkpoint molecule antibodies, antibodies against CTLA-4, PD-L1, OX40, BTLA, GITR, LAG-3, and TIM-3 have especially serious side effects, and that combined use of an anti-CD4 component with these antibodies reduces such serious side effects, and increases the survival rate of the tumor-bearing living body (see the following Examples). As described above, PD-1 is a receptor for PD-L1.

The immune checkpoint regulator may be an antibody against an immune checkpoint molecule. Specific examples of the immune checkpoint regulator include antagonistic antibodies such as an anti-PD-1 antibody, anti-CTLA-4 antibody, anti-LAG-3 antibody, anti-TIM-3 antibody and an anti-BTLA antibody, which bind to a receptor to inhibit binding of a ligand to the receptor; and agonistic antibodies such as an anti-CD137 antibody, anti-OX40 antibody and an anti-GITR antibody, which bind to a receptor to stimulate a downstream signaling pathway. Other specific examples of the immune checkpoint regulator include an anti-PD-L1 antibody, anti-PD-L2 antibody, anti-GAL9 antibody and an anti-HVEM antibody, which bind to a ligand for an inhibitory immune checkpoint receptor to inhibit binding of the ligand to the receptor. Preferred specific examples of the immune checkpoint regulator include, but are not limited to, an anti-PD-L1 antibody, antagonistic anti-CTLA-4 antibody, and an agonistic anti-OX40 antibody. Other preferred specific examples include, but are not limited to, an anti-CD137 antibody.

As described above, immune checkpoint regulators are typically used as an anticancer drug. Immune checkpoint regulators are thought to be effective for any kind of cancer because of their action mechanism. As for the administration route and the dose of the immune checkpoint regulator, for example, those conventionally employed when the immune checkpoint regulator is used as an anticancer drug may also be used in the present invention. By using an immune checkpoint regulator in combination with an anti-CD4 component, a sufficient therapeutic effect can be obtained without largely reducing the dose of the immune checkpoint regulator even in cases where there is a concern that serious side effects may be caused by the immune checkpoint regulator.

The term "combined use" or "used in combination" means that a plurality of agents are administered concurrently, sequentially, or separately, to a patient. The plurality of agents to be used in combination may be provided as separate formulations. In cases where they are administered concurrently, a plurality of agents may be contained in a single formulation.

The number of the immune checkpoint regulator used in combination with the anti-CD4 component is not limited. One immune checkpoint regulator may be used, or two immune checkpoint regulators may be used, or three or more immune checkpoint regulators may be used, in combination with the anti-CD4 component.

Preferred specific examples of the combination include the combination of the following three components: an anti-CD4 component, an antagonistic anti-PD-1 antibody, and an antagonistic anti-CTLA-4 antibody; and the combination of the following three components: an anti-CD4 component, an anti-PD-L1 antibody, and an antagonistic anti-CTLA-4 antibody. However, the combinations of antibodies which can be used in the present invention are not limited to those described above.

The administration route of the anti-CD4 component may be oral or parenteral, and parenteral administration such as intramuscular administration, subcutaneous administration, intravenous administration, or intraarterial administration is preferred. In cases where the immune checkpoint regulator is used as an anticancer drug for a solid cancer, the anti-CD4 component may be locally administered to the vicinity of the solid cancer tissue, or may be administered to a regional lymph node in the vicinity of the solid cancer. Systemic administration is preferred.

The dose of the anti-CD4 component may be administered at any dose as long as it is effective for reducing a side effect(s) of the immune checkpoint regulator. The effective dose is appropriately selected depending on symptoms of the disease to be treated by the immune checkpoint regulator (in cases of cancer, tumor size, symptoms, etc.), age and body weight of the patient, and the like. The dose of the anti-CD4 component may be, but not limited to, about 0.001 mg/kg to 1000 mg/kg, e.g., about 0.01 mg/kg to 100 mg/kg, in terms of the weight of the effective ingredient per day per 1 kg body weight of the patient. The above-described dose may be given to a patient once or dividedly in a few or several times in a day. During the period of the treatment with the immune checkpoint regulator, the anti-CD4 component may be administered once, or daily for a few or several days, or may be administered multiple times every few or several days, every few or several weeks, or every few or several months. Administration of the anti-CD4 component may be carried out before the beginning of the administration of the immune checkpoint regulator.

The subject patient in the present invention is a mammal, which is typically human. The patient is typically a cancer patient. The patient is a patient receiving administration of an immune checkpoint regulator, or a patient who is going to receive administration of an immune checkpoint regulator.

The anti-CD4 component can be formulated by appropriately mixing with additives such as pharmaceutically acceptable carriers, diluents, and/or excipients that are suitable for the administration route employed. Examples of the formulation include oral preparations such as tablets, capsules, granules, powders, and syrups; and parenteral preparations such as inhalants, injection solutions, suppositories, and solutions. Formulation methods and additives which can be used are well known in the field of formulation of pharmaceuticals, and any of the methods and additives may be used.

EXAMPLES

The present invention is described below by way of Examples more concretely. However, the present invention is not limited to the Examples described below.

Example 1: Preparation of Anti-CD4 Humanized Antibody Having High ADCC Activity

According to the method described in WO 2010/074266, an anti-human CD4 humanized antibody IT1208 having enhanced ADCC activity (wherein HV2 and LV0 described in WO 2010/074266 are contained as the variable region; subtype, IgG1) was prepared. The antibody binding activity as measured using Biacore T100 was $K_D$ (nM)<0.009, which indicates high binding activity.

Measurement of the ADCC activity of IT1208 was carried out under the following conditions, according to the protocol for an ADCC activity assay kit sold by Promega. After gently mixing 12,500 PBMCs derived from a healthy individual, anti-CD4 mAb (IT1208), and 75,000 ADCC Bioassay Effector cells contained in the Promega kit, the cells were cultured in a $CO_2$ incubator at 37° C. for 6 hours. The luminescent reagent Bio-Glo reagent was added to the culture, and culturing was then continued at room temperature for 20 minutes, followed by measuring chemiluminescence using a luminescence plate reader.

Figure 1:
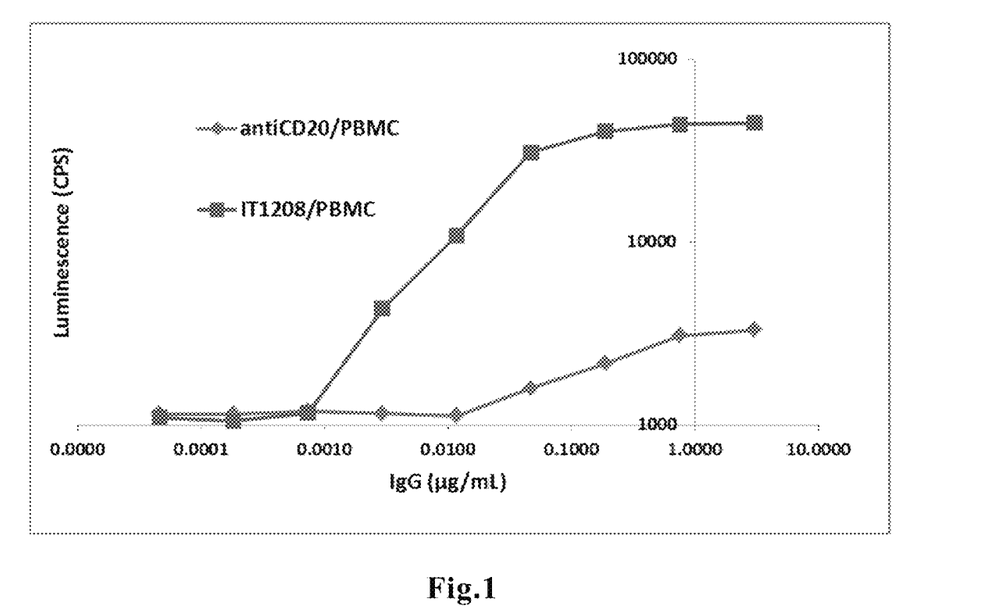
FIG. 1 shows the ADCC activity of an anti-CD4 humanized antibody IT1208 against CD4-positive cells in human peripheral blood mononuclear cells measured by using a commercially-available assay kit.

The results are shown in FIG. 1. IT1208 showed ADCC activity at 1 nM or more, and the activity then increased concentration-dependently to reach the maximum value at 50 nM. In the cases of Rituximab (anti-CD20), which was used as a control antibody, the concentration at which the ADCC activity began to be found was 10 nM or more, and the concentration at which the maximum value was achieved was 1 µM or more.

Example 2-1: Antitumor Effect by Combined Use of Anti-CD4 Antibody+Immune

Checkpoint Antibody on Melanoma Cells (Part 1)

The mouse melanoma cell line B16F10 ($5 \times 10^5$ cells/mouse) was subcutaneously transplanted into the right abdomen of C57BL/6 mice (female, 7 weeks old, n=8), and antibody administration was carried out as described below (Day 0=day of cancer cell transplantation). As an immune checkpoint antibody, an anti-PD-1 antibody (J43, antagonistic antibody, manufactured by BioXcell), anti-PD-L1 antibody (10F.9G2, manufactured by BioXcell), anti-OX40 antibody (OX-86, agonistic antibody, manufactured by BioXcell), and anti-CTLA-4 antibody (9D9, antagonistic antibody, manufactured by BioXcell) were used.

TABLE 1

| | |
|---|---|
| Negative control group | No antibody is administered. (A solvent PBS is administered.) |
| Anti-CD4 alone group | An anti-CD4 antibody (0.2 mg; GK1.5, an antibody known to be capable of depleting CD4-positive cells in the mouse body by the CDC activity; manufactured by BioXcell) is intraperitoneally administered twice on Day 5 and Day 9. |
| Anti-immune checkpoint antibody alone group | Any one of anti-immune checkpoint antibodies (0.2 mg) is intraperitoneally administered on Day 4, Day 8, Day 14, and Day 18, four times in total. |
| Anti-CD4 + immune checkpoint antibody combination group | An anti-CD4 antibody (0.2 mg) is intraperitoneally administered twice on Day 5 and Day 9, and any one of anti-immune checkpoint antibodies (0.2 mg) is intraperitoneally administered on Day 4, Day 8, Day 14, and Day 18, four times in total. |

Figure 2:
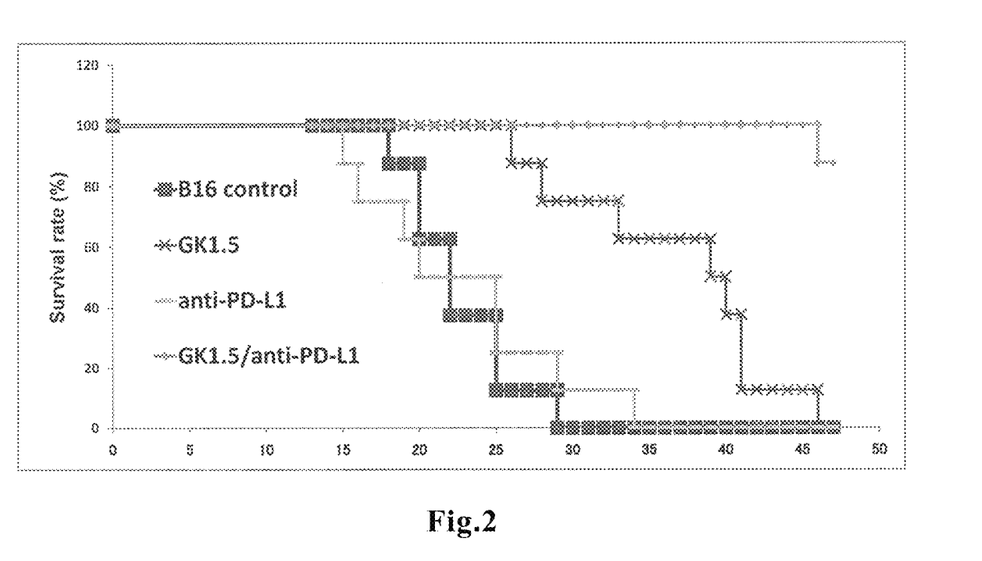
FIG. 2 shows the survival rate in each antibody administration group of C57BL/6 mice transplanted with the B16F10 cell line (comparison between administration of an anti-PD-L1 antibody alone and combined administration of the anti-PD-L1 antibody + an anti-CD4 antibody GK1.5).
Figure 3:
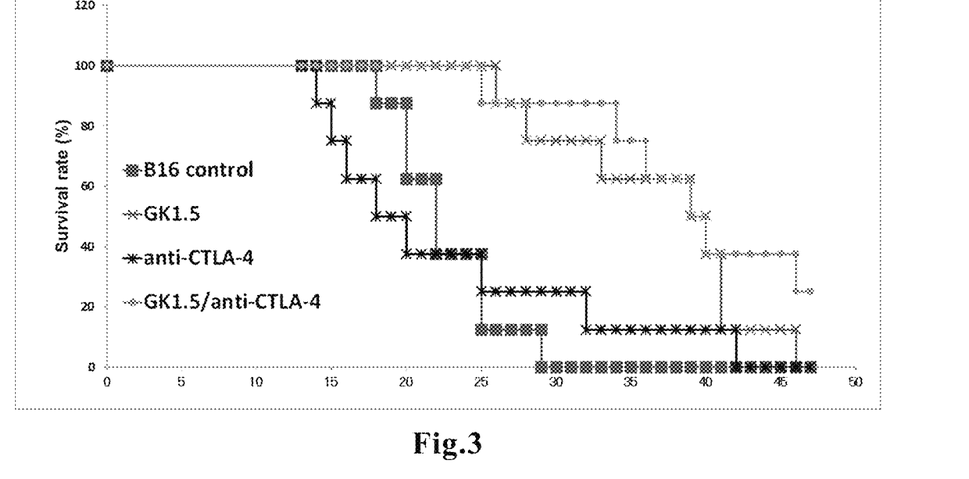
FIG. 3 shows the survival rate in each antibody administration group of C57BL/6 mice transplanted with the B16F10 cell line (comparison between administration of an anti-CTLA-4 antibody alone and combined administration of the anti-CTLA-4 antibody + an anti-CD4 antibody GK1.5).
Figure 4:
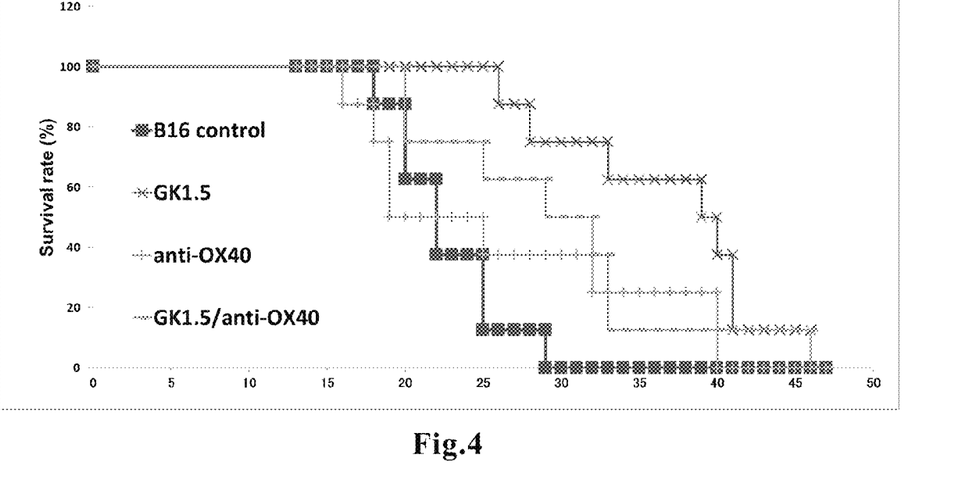
FIG. 4 shows the survival rate in each antibody administration group of C57BL/6 mice transplanted with the B16F10 cell line (comparison between administration of an anti-OX40 antibody alone and combined administration of the anti-OX40 antibody + an anti-CD4 antibody GK1.5).

FIGS. 2 to 4 show the survival rate in each group of C57BL/6 mice transplanted with the B16F10 cell line.

Figure 5:
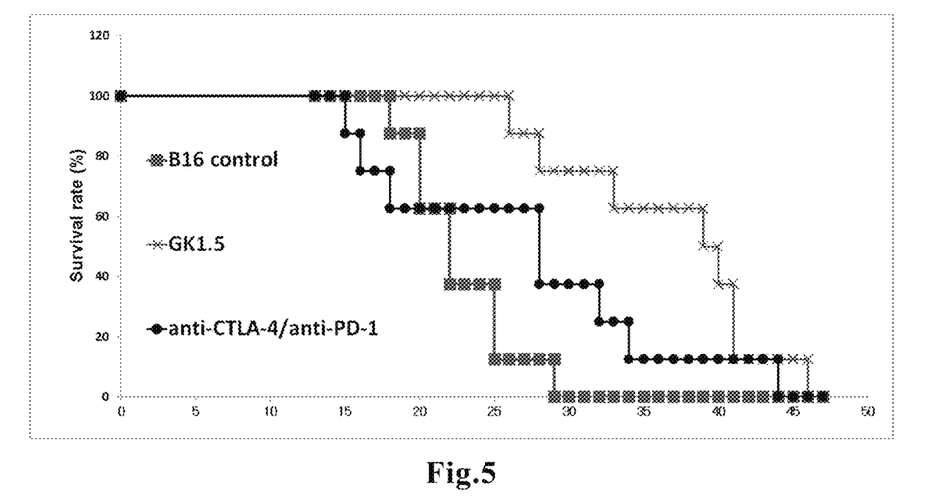
FIG. 5 shows the survival rate in each antibody administration group of C57BL/6 mice transplanted with the B16F10 cell line (combined administration of an anti-CTLA-4 antibody + an anti-PD-1 antibody).
Figure 6:
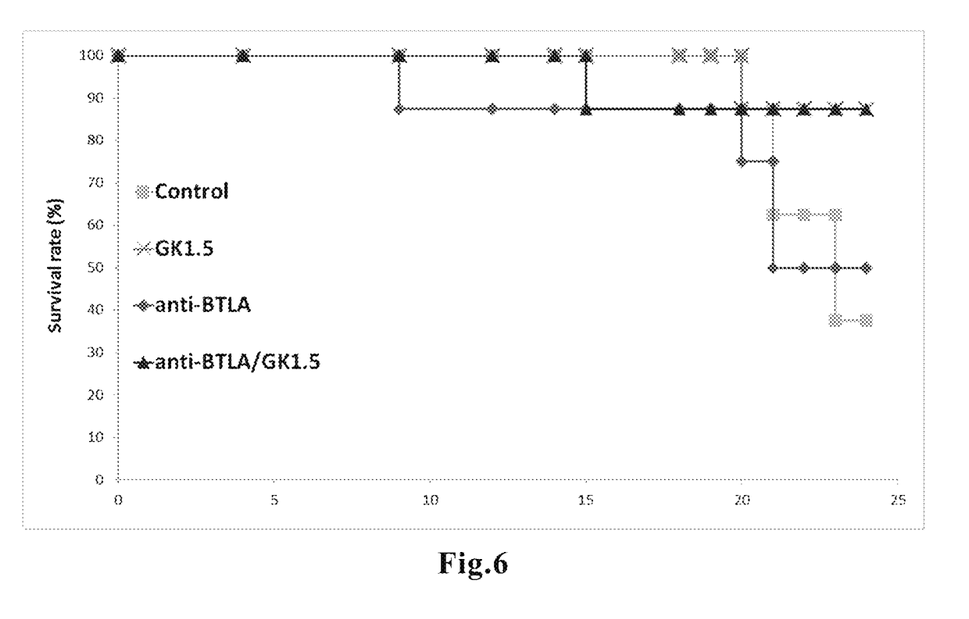
FIG. 6 shows the survival rate in each antibody administration group of C57BL/6 mice transplanted with the B16F10 cell line (comparison between administration of an anti-BTLA antibody alone and combined administration of the anti-BTLA antibody + an anti-CD4 antibody GK1.5).
Figure 7:
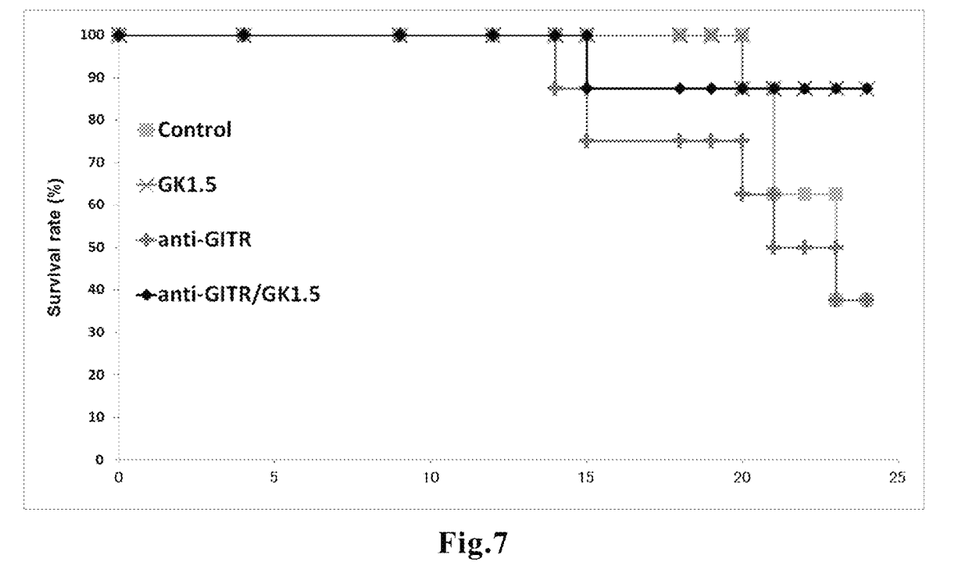
FIG. 7 shows the survival rate in each antibody administration group of C57BL/6 mice transplanted with the B16F10 cell line (comparison between administration of an anti-GITR antibody alone and combined administration of the anti-GITR antibody + an anti-CD4 antibody GK1.5).
Figure 8:
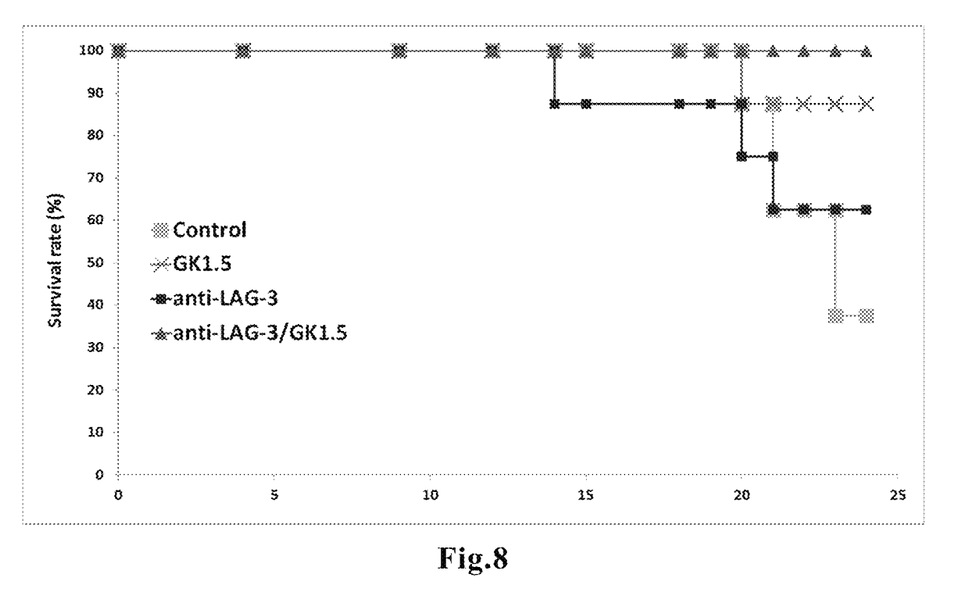
FIG. 8 shows the survival rate in each antibody administration group of C57BL/6 mice transplanted with the B16F10 cell line (comparison between administration of an anti-LAG-3 antibody alone and combined administration of the anti-LAG-3 antibody + an anti-CD4 antibody GK1.5).
Figure 9:
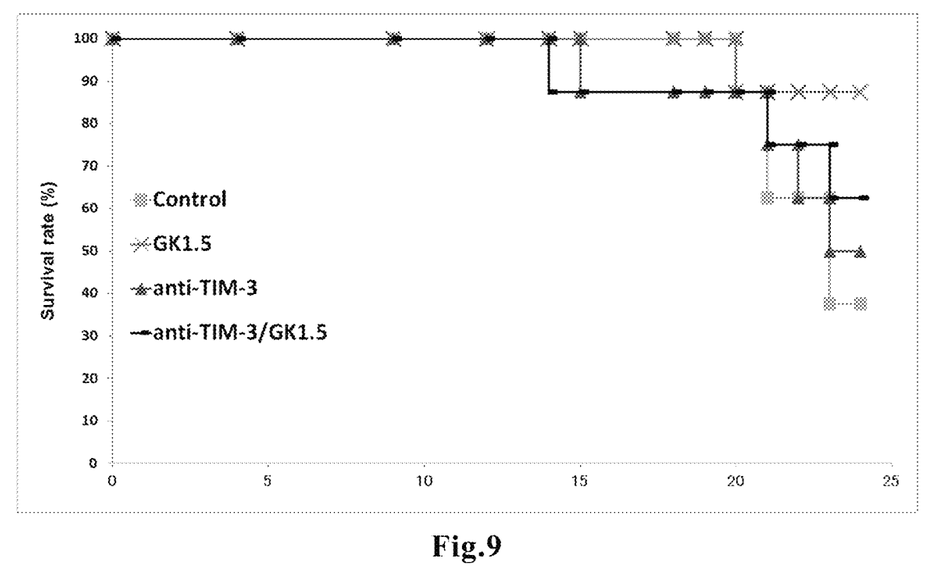
FIG. 9 shows the survival rate in each antibody administration group of C57BL/6 mice transplanted with the B16F10 cell line (comparison between administration of an anti-TIM-3 antibody alone and combined administration of the anti-TIM-3 antibody + an anti-CD4 antibody GK1.5).

In the groups receiving the anti-PD-L1 antibody, anti-OX40 antibody, or anti-CTLA-4 alone, one to three death cases occurred earlier than in the control group. Such an increase in the death cases were also found in the group receiving combined use of the anti-PD-1 antibody (J43, antagonistic antibody, manufactured by BioXcell) and the anti-CTLA-4 antibody (FIG. 5).

In contrast, combined use of the anti-CD4 antibody with the anti-PD-L1 antibody, anti-OX40 antibody, or anti-CTLA-4 antibody remarkably improved the survival rate. Thus, it became clear that side effects due to the immune checkpoint antibodies can be remarkably reduced by using the anti-CD4 antibody in combination.

Example 2-2: Antitumor Effect by Combined Use of Anti-CD4 Antibody+Immune Checkpoint Antibody on Melanoma Cells (Part 2)

The mouse melanoma cell line B16F10 ($5\times10^5$ cells/mouse) was subcutaneously transplanted into the right abdomen of C57BL/6 mice (female, 7 weeks old, n=8), and antibody administration was carried out as described below (Day 0=day of cancer cell transplantation). As an immune checkpoint antibody, an anti-BTLA antibody (6A6, antagonistic antibody, manufactured by BioXcell), anti-GITR antibody (DTA-1, agonistic antibody, manufactured by BioXcell), anti-LAG-3 antibody (C9B7W, antagonistic antibody, manufactured by BioXcell), and anti-TIM-3 antibody (RMT3-23, antagonistic antibody, manufactured by BioXcell) were used.

TABLE 2

| | |
|---|---|
| Negative control group | No antibody is administered. (A solvent PBS is administered.) |
| Anti-CD4 alone group | An anti-CD4 antibody (0.2 mg; GK1.5, an antibody known to be capable of depleting CD4-positive cells in the mouse body by the CDC activity; manufactured by BioXcell) is intraperitoneally administered twice on Day 5 and Day 9. |
| Anti-immune checkpoint antibody alone group | Any one of anti-immune checkpoint antibodies (0.2 mg) is intraperitoneally administered on Day 4, Day 8, Day 14, and Day 18, four times in total. |

TABLE 2-continued

| | |
|---|---|
| Anti-CD4 + immune checkpoint antibody combination group | An anti-CD4 antibody (0.2 mg) is intraperitoneally administered twice on Day 5 and Day 9, and any one of anti-immune checkpoint antibodies (0.2 mg) is intraperitoneally administered on Day 4, Day 8, Day 14, and Day 18, four times in total. |

FIGS. 6 to 10 show the survival rate in each group of C57BL/6 mice transplanted with the B16F10 cell line.

Figure 10:
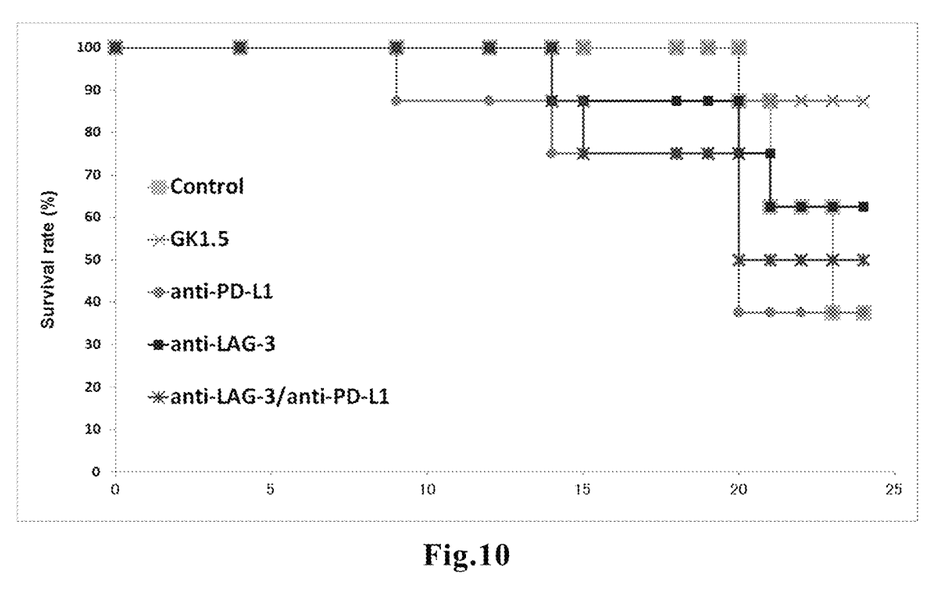
FIG. 10 shows the survival rate in each antibody administration group of C57BL/6 mice transplanted with the B16F10 cell line (combined administration of an anti-PD-L1 antibody + an anti-LAG-3 antibody).

In the groups receiving the anti-BTLA antibody, anti-GITR antibody, anti-LAG-3 antibody, or anti-TIM-3 antibody alone, one to three death cases occurred earlier than in the control group. Such an increase in the death cases was also found in the group receiving combined use of the anti-PD-L1 antibody (10F.9G2, manufactured by BioXcell) and the anti-LAG-3 antibody (without use of the anti-CD4 antibody) (FIG. 10).

In contrast, combined use of the anti-CD4 antibody with the anti-BTLA antibody, anti-GITR antibody, anti-LAG-3 antibody, or anti-TIM-3 antibody remarkably improved the survival rate. Thus, it became clear that side effects due to the immune checkpoint antibodies can be remarkably reduced by using the anti-CD4 antibody in combination.

Example 3: Antitumor Effect by Combined Use of Anti-CD4 Antibody+Immune Checkpoint Antibody on Renal Cancer Cells A mouse renal cancer cell line Renca ($2\times10^5$ cells/mouse) was subcutaneously transplanted into the right abdomen of BALB/c mice (male, 8 weeks old, n=9). Thereafter, antibody administration was carried out as follows (Day 0=day of cancer cell transplantation). As an immune checkpoint antibody, an anti-PD-1 antibody (J43, antagonistic antibody, manufactured by BioXcell) and an anti-PD-L1 antibody (10F.9G2, manufactured by BioXcell) were used.

TABLE 3

| | |
|---|---|
| Negative control group | No antibody is administered. (A solvent PBS is administered.) |
| Anti-CD4 alone group | An anti-CD4 antibody (0.2 mg; GK1.5, an antibody known to be capable of depleting CD4-positive cells in the mouse body by the CDC activity; manufactured by BioXcell) is intraperitoneally administered twice on Day 5 and Day 9. |
| Anti-immune checkpoint antibody alone group | Any one of anti-immune checkpoint antibodies (0.2 mg) is intraperitoneally administered on Day 4, Day 8, Day 14, and Day 18, four times in total. |
| Anti-CD4 + immune checkpoint antibody combination group | An anti-CD4 antibody (0.2 mg) is intraperitoneally administered twice on Day 5 and Day 9, and any one of anti-immune checkpoint antibodies (0.2 mg) is intraperitoneally administered on Day 4, Day 8, Day 14, and Day 18, four times in total. |

Figure 11:
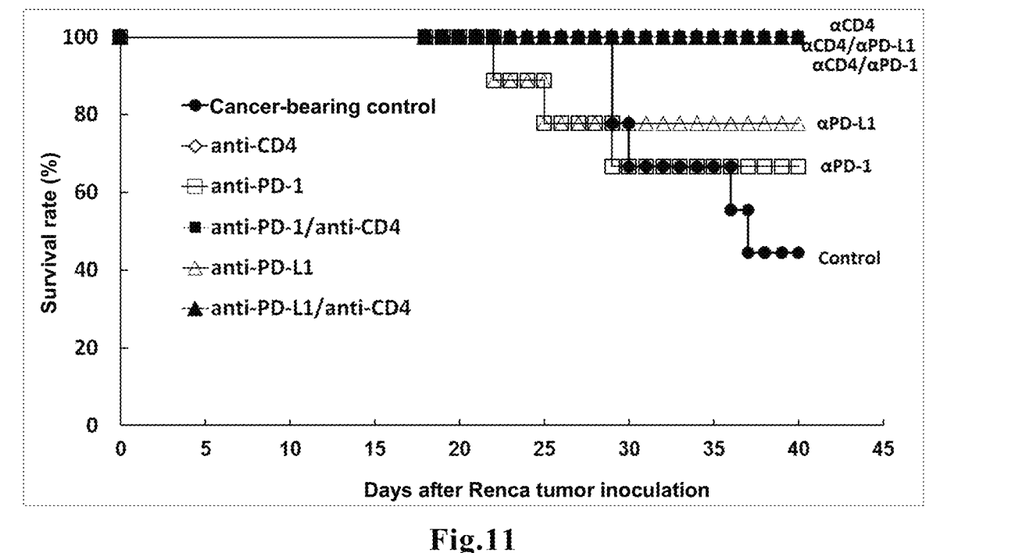
FIG. 11 shows the survival rate in each antibody administration group of BALB/c mice transplanted with the Renca cell line (comparison between administration of an anti-PD-1 antibody or an anti-PD-L1 antibody alone and combined administration with an anti-CD4 antibody GK1.5).

FIG. 11 shows the survival rate in each group of BALB/c mice transplanted with the Renca cell line.

In the groups receiving the anti-PD-1 antibody or the anti-PD-L1 antibody alone, one or two death cases occurred earlier than in the control group.

In contrast, combined use of the anti-CD4 antibody with the anti-PD-1 antibody or the anti-PD-L1 antibody remarkably improved the survival rate. Thus, it became clear that side effects due to the immune checkpoint antibodies can be remarkably reduced by using the anti-CD4 antibody in combination.

Example 4: Antitumor Effect by Combined Use of
Anti-CD4 Antibody+Immune Checkpoint Antibody
on Breast Cancer Cells A mouse breast cancer cell line 4T1 ($1 \times 10^5$ cells/mouse) was transplanted into the mammary fat pad of BALB/c mice (female, 8 weeks old, n=10), and antibody administration was carried out as follows (Day 0=day of cancer cell transplantation). As an immune checkpoint antibody, an anti-PD-1 antibody (J43, antagonistic antibody, manufactured by BioXcell) and an anti-PD-L1 antibody (10F.9G2, manufactured by BioXcell) were used.

TABLE 4

| | |
|---|---|
| Negative control group | No antibody is administered. (A solvent PBS is administered.) |
| Anti-CD4 alone group-(1) | An anti-CD4 antibody (0.2 mg; GK1.5, an antibody known to be capable of depleting CD4-positive cells in the mouse body by the CDC activity; manufactured by BioXcell) is intraperitoneally administered twice on Day 5 and Day 9. |
| Anti-CD4 alone group-(2) | An anti-CD4 antibody (0.2 mg; GK1.5, manufactured by BioXcell) is intraperitoneally administered twice on Day 13 and Day 17. |
| Anti-immune checkpoint antibody alone group | Any one of anti-immune checkpoint antibodies (0.2 mg) is intraperitoneally administered on Day 4, Day 8, Day 14, and Day 18, four times in total. |
| Anti-CD4 + immune checkpoint antibody combination group | An anti-CD4 antibody (0.2 mg) is intraperitoneally administered twice on Day 5 and Day 9, and any one of anti-immune checkpoint antibodies (0.2 mg) is intraperitoneally administered on Day 4, Day 8, Day 14, and Day 18, four times in total. |

Table 5 shows the allergic symptoms observed in each group of BALB/c mice transplanted with the 4T1 cell line. Symptoms observed during the two hours following the third administration on Day 14 were evaluated. Each value in the table represents the number of mouse individuals.

TABLE 5

Evaluation of Anaphylaxis Caused by Anti-PD-1 Antibody or Anti-PD-L1 Antibody, and Inhibitory Action by Anti-CD4 Antibody in 4T1 Tumor-bearing Mice (Day 14)

| | Decreased body temperature | | | Sedation (decreased activity) | | |
|---|---|---|---|---|---|---|
| | − | + | +++ | − | + | +++ |
| Control group | 10 | 0 | 0 | 10 | 0 | 0 |
| Anti-CD4 | 10 | 0 | 0 | 10 | 0 | 0 |
| Anti-PD-1 | 0 | 1 | 9 | 0 | 0 | 10 |
| Anti-CD4/Anti-PD-1 | 10 | 0 | 0 | 0 | 0 | 0 |
| Anti-PD-L1 | 0 | 2 | 8 | 0 | 0 | 10 |
| Anti-CD4/Anti-PD-L1 | 9 | 1 | 0 | 0 | 0 | 0 |

| Evaluation criteria | Decreased body temperature | Decreased activity |
|---|---|---|
| − | Normal (equivalent to the control group) | Normal |
| + | Cold | Slow moving |
| +++ | No feeling of body temperature | No movement even being touched; standstill |

All mice receiving the anti-PD-1 antibody or the anti-PD-L1 antibody alone began to show serious anaphylaxis at several minutes or more after the third administration on Day 14 or the forth administration on Day 18, and a part or all of the mice died. All the deaths occurred within two hours after the administration. The surviving mice recovered over several hours thereafter.

In the control group and the anti-CD4 alone group, a solvent PBS and the anti-CD4 antibody were intraperitoneally administered to mice in a similar manner, but neither allergic symptoms nor death cases occurred.

The fact that anaphylaxis occurs in the 4T1 tumor mouse model has been confirmed by an active cutaneous anaphylaxis test using Evans Blue which was separately and preliminarily carried out by the present inventors (data not shown), and has also been reported by another group in an academic conference.

In contrast, in mice receiving combined use of the anti-CD4 antibody with the anti-PD-1 antibody or the anti-PD-L1 antibody, a decrease in the body temperature and a decrease in the activity, which are main symptoms of allergic symptoms, were remarkably ameliorated. Thus, it became clear that the side effects due to the immune checkpoint antibodies can be remarkably reduced by combined use of the anti-CD4 antibody.

Figure 12:
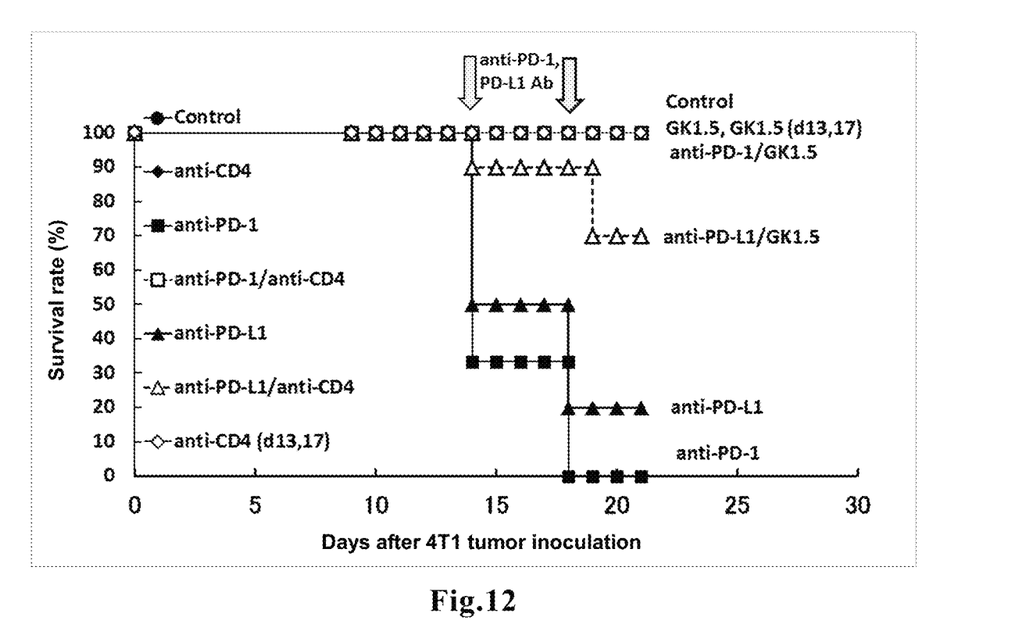
FIG. 12 shows the survival rate in each antibody administration group of BALB/c mice transplanted with the 4T1 cell line (comparison between administration of an anti-PD-1 antibody or an anti-PD-L1 antibody alone and combined administration with an anti-CD4 antibody GK1.5).

FIG. 12 shows the survival rate in each group of BALB/c mice transplanted with the 4T1 cell line.

In the group receiving the anti-PD-1 antibody alone, seven mice died after the third administration on Day 14, and three mice died after the forth administration on Day 18. In the group receiving the anti-PD-L1 antibody alone, five mice died after the third administration on Day 14, and three mice died after the forth administration on Day 18. These deaths were due to anaphylaxis which occurred in all of the antibody-administered mice at several minutes or more after the administration. All the deaths occurred within two hours after the administration. The surviving mice recovered over several hours thereafter.

In the control group and the anti-CD4 alone group, a solvent PBS and the anti-CD4 antibody were intraperitoneally administered to mice in a similar manner, but neither allergic symptoms nor death cases occurred.

In contrast, mice receiving combined use of the anti-CD4 antibody with the anti-PD-1 antibody or the anti-PD-L1 antibody showed remarkable improvement of the survival rate. In the combination group with the anti-PD-1 antibody, all mice survived. In the combination group with the anti-PD-L1 antibody, dead cases decreased; one mouse died after the administration on Day 14, and two mice died after the administration on Day 18. Finally seven mice survived. Thus, it became clear that the side effects due to the immune checkpoint antibodies can be remarkably reduced by combined use of the anti-CD4 antibody.

The invention claimed is:

1. A method for reducing one or more potentially lethal, anaphylactic side effects of an immune checkpoint regulator, said method comprising:
    administering to a cancer patient in need of reducing one or more potentially lethal, anaphylactic side effects of the immune checkpoint regulator, in combination with the immune checkpoint regulator, an effective amount of an anti-CD4 antibody or antigen-binding fragment to deplete CD4-positive immune cells, said antibody or fragment being selected from:
    1) an anti-CD4 antibody having an ADCC activity higher than the ADCC activity of the known anti-CD4 antibodies 6G5 and CE9.1 and/or a CDC activity that is higher than the CDC activity of the known anti-CD4 antibody OKT4, or 2) an anti-CD4 antibody or antigen-binding fragment thereof which antibody or fragment comprises a cytotoxic component bound thereto, wherein said 1) anti-CD4 antibody and said 2) anti-CD4 antibody or antigen-binding fragment thereof is a human-type chimeric antibody, humanized antibody, or human antibody against human CD4;

wherein said immune checkpoint regulator is at least one antagonist against an inhibitory immune checkpoint molecule selected from PD-L1, CTLA-4, BTLA, LAG-3, TIM-3, and PD-1;

wherein said cancer is selected from cancers other than melanoma;

wherein in said method, first administration of the anti-CD4 antibody or the antigen-binding fragment is not carried out before first administration of the immune checkpoint regulator, and is carried out before second administration of the immune checkpoint regulator; and wherein the effective amount of the anti-CD4 antibody or antigen-binding fragment is sufficient to reduce one or more potentially lethal, anaphylactic side effects of the immune checkpoint regulator.

2. The method according to claim 1, wherein said inhibitory immune checkpoint molecule is at least one selected from the group consisting of CTLA-4, PD-L1, BTLA, LAG-3 and TIM-3.

3. The method according to claim 1, wherein said immune checkpoint regulator is an antibody against an inhibitory immune checkpoint molecule.

4. The method according to claim 3, wherein said antibody against an inhibitory immune checkpoint molecule is at least one selected from an anti-PD-L1 antibody, and antagonistic anti-CTLA-4 antibody.

5. The method according to claim 3, wherein said antibody against an inhibitory immune checkpoint molecule is at least one selected from an antagonistic anti-BTLA antibody, antagonistic anti-LAG-3 antibody, and an antagonistic anti-TIM-3 antibody.

6. The method according to claim 1, which comprises administering an effective amount of an anti-CD4 antibody having an ADCC activity higher than the ADCC activity of the known anti-CD4 antibodies 6G5 and CE9.1 and/or a CDC activity that is higher than the CDC activity of the known anti-CD4 antibody OKT4.

7. A method for cancer therapy by combination therapy with depletion of CD4-positive immune cells and one or more immune checkpoint regulators, said method comprising:

administering in combination with said one or more immune checkpoint regulators to a cancer patient in need thereof an effective amount of an anti-CD4 antibody or antigen-binding fragment to deplete CD4-positive immune cells, said antibody or fragment being selected from:

1) an anti-CD4 antibody having an ADCC activity higher than the ADCC activity of the known anti-CD4 antibodies 6G5 and CE9.1 and/or a CDC activity that is higher than CDC activity of the known anti-CD4 antibody OKT4, or 2) an anti-CD4 antibody or antigen-binding fragment thereof which antibody or fragment comprises a cytotoxic component bound thereto, wherein said 1) anti-CD4 antibody and said 2) anti-CD4 antibody or antigen binding fragment thereof are a human-type chimeric antibody, humanized antibody, or human antibody against human CD4;

wherein said immune checkpoint regulator is at least one antagonist against inhibitory immune checkpoint molecule selected from PD-L1, CTLA-4, BTLA, LAG-3, TIM-3, and PD-1;

wherein said cancer is selected from cancers other than melanoma;

wherein in said combination therapy, first administration of the anti-CD4 antibody or the antigen-binding fragment is not carried out before first administration of the immune checkpoint regulator, and is carried out before second administration of the immune checkpoint regulator; and wherein the effective amount of the anti-CD4 antibody or antigen-binding fragment is sufficient to reduce a potentially lethal, anaphylactic side effect of the one or more immune checkpoint regulators, thereby improving survival rate of the cancer patient.

8. The method according to claim 7, which comprises administering an effective amount of 1) an anti-CD4 antibody having an ADCC activity higher than the ADCC activity of the known anti-CD4 antibodies 6G5 and CE9.1 and/or a CDC activity that is higher than the CDC activity of the known anti-CD4 antibody OKT4.

9. The method according to claim 7, wherein said antibody 1) is an anti-CD4 antibody which contains no core fucoses in sugar chains present in its Fc region.

10. The method according to claim 1, wherein said antibody 1) is an anti-human CD4 humanized antibody IT1208.

11. The method according to claim 7, wherein said antibody 1) is an anti-human CD4 humanized antibody IT1208.

12. The method according to claim 7, wherein said inhibitory immune checkpoint molecule is at least one selected from the group consisting of PD-L1, CTLA-4, BTLA, LAG-3 and TIM-3.

13. The method according to claim 12, wherein said inhibitory immune checkpoint molecule is selected from PD-L1, CTLA-4, LAG-3, and PD-1.

14. The method according to claim 1, wherein the cancer is selected from renal cancer, breast cancer, lung cancer, and gastric cancer.

15. The method according to claim 7, wherein the cancer is selected from renal cancer, breast cancer, lung cancer, and gastric cancer.

* * * * *